US006653274B1

(12) United States Patent  
Godfroid et al.

(10) Patent No.: US 6,653,274 B1
(45) Date of Patent: Nov. 25, 2003

(54) DETERGENT COMPOSITION COMPRISING A SOIL ENTRAINMENT SYSTEM

(75) Inventors: Robert Allen Godfroid, West Chester, OH (US); Kenneth William Willman, Fairfield, OH (US); Christopher James Binski, Cincinnati, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 103 days.

(21) Appl. No.: 09/655,221

(22) Filed: Sep. 5, 2000

Related U.S. Application Data

(60) Provisional application No. 60/156,289, filed on Sep. 27, 1999.

(51) Int. Cl.$^7$ .............................. C11D 1/00; C11D 3/26; C11D 3/30
(52) U.S. Cl. .................. 510/499; 510/215; 510/217; 510/181; 510/238; 510/421; 510/422; 510/426; 510/427; 510/435; 510/506
(58) Field of Search .............................. 510/214, 215, 510/217, 180, 181, 238, 421, 422, 426, 427, 435, 499, 506

(56) References Cited

U.S. PATENT DOCUMENTS

| | | | |
|---|---|---|---|
| 3,000,830 A | 9/1961 | Long et al. ................. 252/117 |
| 4,175,062 A | * 11/1979 | Disch et al. ................ 252/540 |
| 4,343,725 A | * 8/1982 | Kiewert et al. ............. 252/542 |
| 4,448,704 A | 5/1984 | Barby et al. ................ 252/91 |
| 4,486,329 A | 12/1984 | Ellis et al. .................. 252/117 |
| 4,976,885 A | * 12/1990 | Wisotzki et al. .......... 252/174.17 |
| 5,094,559 A | 3/1992 | Rivera et al. ............... 401/132 |
| 5,419,015 A | 5/1995 | Garcia ........................ 15/228 |
| 5,534,198 A | 7/1996 | Masters et al. ............. 510/182 |
| 5,565,145 A | 10/1996 | Watson et al. .............. 510/350 |
| 5,750,482 A | 5/1998 | Cummings .................. 510/182 |
| 6,045,817 A | 4/2000 | Ananthapadmanabhan et al. .......................... 424/405 |
| 6,083,898 A | * 7/2000 | Meixner et al. ............ 510/499 |

FOREIGN PATENT DOCUMENTS

| | | | |
|---|---|---|---|
| CA | 2004762 | 12/1988 | |
| EP | 0009193 | * 9/1979 | |
| EP | 342997 | 11/1989 | ........... C11D/1/835 |
| EP | 372610 | 11/1989 | ........... C23G/1/14 |
| EP | 859045 | 8/1998 | ........... C11D/3/00 |
| WO | WO 91/00332 | 1/1991 | ........... C11D/3/37 |
| WO | WO 96/18718 A1 | 6/1996 | |
| WO | WO 98/17764 A1 | 4/1998 | |
| WO | WO 98/42819 | 10/1998 | ........... C11D/17/04 |
| WO | WO 98/47993 | 10/1998 | ........... C11D/3/00 |
| WO | WO 99/09135 | 2/1999 | ........... C11D/11/00 |
| WO | WO 99/11746 | 3/1999 | ........... C11D/3/30 |
| WO | WO 99/18182 | 4/1999 | ........... C11D/3/22 |
| WO | WO 99/19449 | 4/1999 | ........... C11D/3/37 |
| WO | WO 99/24539 | 5/1999 | ........... C11D/3/30 |
| WO | WO 00/49122 A1 | 8/2000 | |

* cited by examiner

*Primary Examiner*—Gregory Delcotto
(74) *Attorney, Agent, or Firm*—Ian Robinson; Thibault Fayette; Kim William Zerby

(57) ABSTRACT

The present invention relates to a hard surface detergent composition containing a soil entrainment system. The composition can be used with conventional implements known in the art, including sponges, cloths and/or sponge, string, and/or strip mops and floor cloths such as those sold at retail and specialty stores. In a most preferred embodiment, the solution is used with a cleaning pad comprising an effective amount of a superabsorbent material, said pad preferably being part of a cleaning implement comprising a handle and said cleaning pad preferably being removable. The process of using the detergent composition with such a cleaning pad, and the provision of a kit containing both detergent composition and cleaning pad are disclosed.

32 Claims, No Drawings

DETERGENT COMPOSITION COMPRISING A SOIL ENTRAINMENT SYSTEM

This application claims the benefit of U.S. Provisional Application No. 60/156,289, filed on Sep. 27, 1999.

TECHNICAL FIELD

This application relates to detergent compositions containing a soil entrainment system. The detergent composition cleaning solution is also preferably suitable for use with a disposable cleaning pad. This application also relates to a process of using the detergent composition with such a cleaning pad, and the provision of a kit containing the detergent composition and cleaning pad are disclosed.

BACKGROUND OF THE INVENTION

The developer and formulator of surfactants for hard surface cleaning must consider a wide variety of possibilities with limited (sometimes inconsistent) information, and then strive to provide overall improvements in one or more of a whole array of criteria, including performance in the presence of free calcium and a wide variety of soils, in complex mixtures of surfactants and polymers, e.g. cationic polymers, formulation changes, enzymes, various changes in consumer habits and practices, and the need for biodegradability.

One particularly problematic area is that of the different types of soils. Particulate soils, such as clay, sand, dirt, lint, humic soils, and silicates, are especially problematic. The difficulty with particulate soils is not their dissolution, but rather their removal from the surface. In no rinse situations the particulate soils are suspended, but reappear upon drying as streaking and hazing on the "cleaned surface". Alternatively, rinsing the surface after suspending the particulate soil is not a realistic option, either because of the nature of the surface, e.g. wood which is easily damaged by water, or the impracticality and possible hazards of using large volume of water in cleaning household surfaces near electrical appliance. Wiping the surface with a cloth, sponge mop or the like at best can remove some of the particulate soil. At worst merely redistributing the particulate soil over the surface being cleaned. Floors are particularly susceptible to this redistribution, as the solutions used traditional cleaning methods, i.e. mop with dilute cleaning solution in a bucket, effectively become "dirty water" after a limited application of the mop and solution to the surface. This either require frequent stoppages to refresh the cleaning solution, or that the consumer tolerate surfaces which are streaked and hazy.

Consequently, there remains the need for a hard surface cleaning composition which can readily and conveniently remove particulate soil from a hard surface and prevent their redeposition, without the use of rinsing.

SUMMARY OF THE INVENTION

The present invention meets the aforementioned needs in that it has been surprisingly discovered that a soil entrainment system traps the particulate soil facilitating its removal from the surface, eliminating the need for rinsing the surface.

A first aspect of the present invention relates to an aqueous hard surface cleaning composition that provides effective cleaning and good filming streaking, in combination with a disposable cleaning pad, said combination being suitable for use without rinsing wherein said composition comprises:

a) an effective amount of a soil entrainment system, said soil entrainment system is selected from the group consisting of
1) one or more modified polyamine compounds, said modified polyamine compounds are selected from:
   i) $(PA)_w(T)_x$;
   ii) $(PA)_w(L)_z$;
   iii) $[(PA)_w(T)_x]_y[L]_z$; and
   iv) mixtures thereof;
   wherein PA is a grafted or non-grafted, modified or unmodified polyamine backbone unit, T is an amide-forming polycarboxylic acid crosslinking unit, and L is a non-amide forming crosslinking unit; provided that for compounds of type (i) and (iii) the indices w and x have values such that the ratio of w to x is from 0.8:1 to 1.5:1; for compounds of type (ii) the indices w and z have values such that said modified polyamine compound comprises from about 0.05 to about 2 parts by weight of said L unit; for compounds of type (iii) the indices y and z have values such that said modified polyamine compound comprises from about 0.05 to about 2 parts by weight of said L unit; and
2) polyethylene glycols with an average molecular weight of from about 400,000 daltons to about 15,000,000 daltons;
3) one or more modified polyacrylanide compounds of the formula:

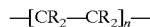

$$-[CR_2-CR_2]_n-$$

wherein each R unit is independently selected from the group consisting of hydrogen, $C_1$–$C_{12}$ alkyl, $C_6$–$C_{12}$ aryl, $CON(R')_2$, and D; wherein each D unit is independently selected from the group consisting of $CO_2N(R')_m$, $CON(R')CH_2CON(R')_2$, $OCON(R')_2$, and $CO_2(CH_2)_qN(R')_m$, wherein each R' is selected from the group consisting of hydrogen, $C_1$–$C_{12}$ alkyl, or both R' units can be taken together to form a ring comprising 4–6 carbon atoms; q is an integer from 0 to 5; m is either 2 or 3 and n is a numbers selected such that said modified polyacrylamide compounds have an average molecular weight of from about 20,000 Daltons to about 10,000,000 Daltons; and
4) mixtures thereof; and b) the balance adjunct ingredients;
wherein said composition has a pH under usage conditions of from about 2 to about 12.

A second aspect of the present invention relates to A kit comprising an implement containing a pad containing superabsorbent material and a detergent composition that that provides effective cleaning and good filming streaking when used with a disposable cleaning pad and without rinsing, comprises:

a) an effective amount of a soil entrainment system, said soil entrainment system is selected from the group consisting of
1) one or more modified polyamine compounds, said modified polyamine compounds are selected from:
   i) $(PA)_w(T)_x$;
   ii) $(PA)_w(L)_z$;
   iii) $[(PA)_x(T)_x]_y[L]_z$; and
   iv) mixtures thereof;
   wherein PA is a grafted or non-grafted, modified or unmodified polyamine backbone unit, T is an amide-forming polycarboxylic acid crosslinking unit, and L is a non-amide forming crosslinking unit; provided that for compounds of type (i) and (iii) the indices w and x have values such that the ratio of w to x is from 0.8:1 to 1.5:1; for compounds of type (ii) the indices w and z have values such that said modified polyamine compound comprises from about 0.05 to about 2 parts by weight of said L unit; for compounds of type (iii) the indices y and z have values such that said modified polyamine compound comprises from about 0.05 to about 2 parts by weight of said L unit; and 2) polyethylene glycols with an average molecular weight of from about 400,000 daltons to about 15,000,000 daltons;

3) one or more modified polyacrylamide compounds of the formula:

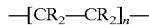
—[CR$_2$—CR$_2$]$_n$— wherein each R unit is independently selected from the group consisting of hydrogen, $C_1$–$C_{12}$ alkyl, $C_6$–$C_{12}$ aryl, CON(R')$_2$, and D; wherein each D unit is independently selected from the group consisting of CO$_2$N(R')$_m$, CON(R')CH$_2$CON(R')$_2$, OCON(R')$_2$, and CO$_2$(CH$_2$)$_q$N(R')$_m$, wherein each R' is selected from the group consisting of hydrogen, $C_1$–$C_{12}$ alkyl, or both R' units can be taken together to form a ring comprising 4–6 carbon atoms; q is an integer from 0 to 5; m is either 2 or 3 and n is a numbers selected such that said modified polyacrylamide compounds have an average molecular weight of from about 20,000 Daltons to about 10,000,000 Daltons; and 4) and mixtures thereof; and b) the balance adjunct ingredients;

and wherein said composition has a pH under usage conditions of from about 2 to about 12.

These and other aspects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to hard surface cleaning compositions which comprise from about 0.001%, preferably from about 0.005%, more preferably from about 0.01%, to about 1.5%, preferably to about 0.5%, more preferably to about 0.1% by weight, of a soil entrainment system. The hard surface cleaning compositions may take any form suitable for use as a hard surface cleaner, for example, solids (i.e., powders, granules, extrudates), gels, thixotropic liquids, liquids (i.e., dispersions, isotropic solutions), preferably the hard surface cleaning compositions take the form of liquids.

Soil Entrainment System

The soil entrainment system of the present invention is comprised of one or more modified polyamine compounds, polyethylene glycols with a specific molecular weight range, one or more modified polyacrylamide compounds and mixtures thereof.

1) Modified polyamine compounds—The soil entrainment system of the present invention may be comprised of one or more modified polyamines according to the present invention. The modified polyamines of the present invention which may comprise the soil entrainment system may be formulated as an admixture wherein a proportional amount of two or more compounds are combined to make up the soil entrainment system. Alternatively, the formulator may adjust the reaction conditions which form the modified polyamines of the present invention in order to create an admixture of suitable ingredients inter alia an admixture of polyamine fragments and/or partially crosslinked modified polyamines. Whether a formulated admixture or a product by process is used, or a mixture of both, the compounds which comprise the soil entrainment system of the present invention have the formula:

(PA)$_w$(T)$_x$;   i)

(PA)$_w$(L)$_z$;   ii)

[(PA)$_w$(T)$_x$]$_y$[L]$_z$;   iii)

wherein PA is a grafted or non-grafted, modified or unmodified polyamine backbone unit, T is an amide-forming polycarboxylic acid crosslinking unit, and L is a non-amide forming crosslinking unit. For compounds of type (i) and (iii) the relative amounts of PA units and T units which are present are such that the molar ratio of PA units to T units is from 0.8:1 to 1.5:1. For compounds of type (ii) the relative amounts of PA units and L units which are present are such that the (PA)$_w$(L)$_z$ comprises from about 0.05, preferably from about 0.3 to 2 parts by weight of said L units. Therefore, 1 part of a grafted or non-grafted, modified or unmodified polyamine backbone unit may be combined with from about 0.05, preferably from about 0.3 parts by weight of an L unit to about 2 parts by weight of an L unit to form a suitable modified polyamine compound. Likewise, for compounds of type (iii), crosslinked polyamines having the formula (PA)$_w$(T)$_x$ may be combined with from about 0.05, preferably from about 0.3 parts by weight of an L unit to about 2 parts by weight of an L unit to form a suitable modified polyamine compound having the formula [(PA)$_w$(T)$_x$]$_y$[L]$_z$, Polyamine Backbone (PA units)

The modified polyamine compounds of the present invention comprise a Polyamine Backbone, PA unit, which can be optionally, but preferably grafted. The following are non-limiting examples of suitable PA units according to the present invention.

Polyalkyleneimine

A preferred PA unit according to the present invention are polyalkyleneimines and polyalkyleneamines having the general formula:

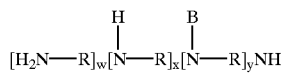

$$[H_2N\text{---}R]_w[\overset{H}{\underset{|}{N}}\text{---}R]_x[\overset{B}{\underset{|}{N}}\text{---}R]_y NH$$

wherein R is $C_2$–$C_{12}$ linear alkylene, $C_3$–$C_{12}$ branched alkylene, and mixtures thereof preferably R is ethylene, 1,3-propylene, and 1,6-hexylene, more preferred is ethylene; B representing a continuation of the chain structure by branching. The indices w, x, and y are such that the molecular weight of said polyamines is from about 50,000 Daltons to about 15,000,000 Daltons, more preferably from about 350,000 Daltons to about 15,000,000 Daltons, even more preferably still from about 600,000 Daltons to about 15,000,000 Daltons. The index w typically has the value of y+1. PA units may be used as crude products or mixtures, and if desired by the formulator, these PA units may be used in the presence of small amounts of diamines as described herein above, wherein the amount of diamines, inter alia, ethylene diamine, hexamethylene diamine may be present up to about 10% by weight, of the PA unit mixture.

Co-polymeric Polyamines

Another example of a preferred PA unit according to the present invention are the polyvinyl amine homo-polymers or co-polymers having the formula:

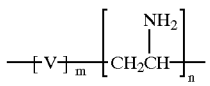

wherein V is a co-monomer, non-limiting examples of which include vinyl amides, vinyl pyrrolidone, vinyl imidazole, vinyl esters, vinyl alcohols, and mixtures thereof, all of which can be taken together or in combination with polyvinyl amine to form suitable co-polymerization products suitable for use in the soil entrainment system of the present invention.

The indices w, x, y, m(when present), and n, when present, are such that the molecular weight of said polyamines is from about 50,000 Daltons to about 15,000,000 Daltons, more preferably from about 350,000 Daltons to about 15,000,000 Daltons, even more preferably still from about 600,000 Daltons to about 15,000,000 Daltons.

Polyamine Backbone Modifications

Optionally, but preferably, the PA units of the present invention are modified either before or after reaction with a T unit or L unit crosslinking agent. The two preferred types of modifications are grafting and capping.

Preferably the PA units of the present invention are grafted, that is the PA unit is further reacted with a reagent which elongates said PA unit chain, preferably by reaction of the nitrogens of the PA backbone unit with one or more equivalents of aziridine (ethyleneimine), caprolactam, and mixtures thereof. Grafting units, in contrast to the "capping" units described herein below, can further react on themselves to provide PA unit chain propagation. An example of a preferred grafted PA unit of the present invention has the formula:

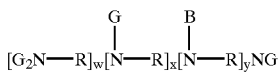

wherein R, B, w, x, and y are the same as defined herein above and G is hydrogen or an extension of the PA unit backbone by grafting. Non-limiting examples of preferred grafting agents are aziridine (ethyleneimine), caprolactam, and mixtures thereof. A preferred grafting agent is aziridine wherein the backbone is extended by units having the formula:

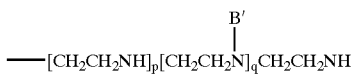

wherein B' is a continuation by branching wherein the graft does not exceed about 12 units, preferably —CH$_2$CH$_2$NH$_2$ and the value of the indices p+q have the value from 0, preferably from about 1, more preferably from about 2 to about 7, preferably to about 5. Another preferred grafting unit is caprolactam.

The PA units of the present invention can be grafted prior to or after crosslinking with one or more T units described herein below, preferably the grafting is accomplished after crosslinking with said T unit. This allows the formulator to take advantage of the differential reactivity between the primary and secondary amino units of the PA unit backbone thereby allowing the formulator to controllably link said PA units and to also control the amount of subsequent branching which results from the grafting step.

Another optional but preferred PA unit modification is the presence of "capping" units. For example, a PA unit is reacted with an amount of a monocarboxylic acid, non-limiting examples of which are $C_1$–$C_{22}$ linear or branched alkyl, preferably $C_{10}$–$C_{18}$ linear alkyl inter alia lauric acid, myristic acid. The amount of capping unit which is reacted with the PA unit is an amount which is sufficient to achieve the desired properties of the formula. However, the amount of capping unit used is not sufficient to abate any further crosslinking or grafting which the formulator may choose to perform.

Crosslinking Units

Amide-forming T Crosslinking Units

T crosslinking units are preferably carbonyl comprising polyamido forming units. The T units are taken together with PA units to form crosslinked modified polyamine compounds having the formula $(PA)_w(T)_x$ or $[(PA)_w(T)_x]_y[L]_z$.

A preferred embodiment of the present invention includes crosslinked PA units wherein a T unit provides crosslinking between two or more PA units to form a $(PA)_w(T)_x$ polyamido crosslinked section. A preferred crosslinking T unit has the general formula:

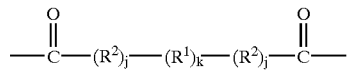

wherein $R^1$ is methylene, phenylene, and mixtures thereof; preferably methylene. The index k has the value from 2 to about 8, preferably to about 4. Preferred values of k are 2, 3, and 4. $R^2$ is —NH— thereby forming a urethane amide linkage when said $R^2$ comprising T units react with the backbone nitrogens of the PA units. The value of the index j is independently 0 or 1. The presence of $R^2$ units can result, for example, from the use of diisocyanates as crosslinking agents. Non-limiting examples of dibasic acids which are used as a source for T units in the above formula include succinic acid, maleic acid, adipic acid, glutaric acid, suberic acid, sebacic acid, and terephthalic acid. However, the formulator is not limited to crosslinking T units deriving from dibasic acids, for example, tribasic crosslinking T units, inter alia, citrate, may be used to link the PA units of the present invention.

Examples of $(PA)_w(T)_x$ compounds according to the present invention are obtained by condensation of dicarboxylic acids inter alia succinic acid, maleic acid, adipic acid, terephthalic acid, with polyalkylene polyamines inter alia diethylenetriamine, triethylenetetramine, dipropylenetriamine, tripropylenetetramine wherein the ratio of the dicarboxylic acid to polyalkyleneamine is from 1:0.8 to 1:1.5 moles, preferably a ratio of from 1:0.9 to 1:1.2 moles wherein the resulting crosslinked material has a viscosity in a 50% by weight, aqueous solution of more than 100 centipoise at 25° C.

Non-amide Forming L Crosslinking Units

Another preferred embodiment of the polyamines of the present invention are $(PA)_w(T)_x$ units which are further crosslinked by L units to form polyamido amines having the formula $[(PA)_w(T)_x]_y[L]_z$ or are reacted with PA units to form non-amide polyamines having the formula $(PA)_w(L)_z$.

The L units of the present invention are any unit which suitably crosslinks PA units or $(PA)_w(T)_x$ units. Preferred L linking units comprise units which are derived from the use of epihalohydrins, preferably epichlorohydrin, as a crosslinking agent. The epihalohydrins can be used directly with the PA units or suitably combined with other crosslinking adjuncts non-limiting examples of which include alkyleneglycols, and polyalkylene polyglycols inter alia ethylene glycol, diethylene glycol, polyethylene glycol, propylene glycol, dipropylene glycol, polypropylene glycol, butylene glycol, hexanediol-1,6-glycerol, oligoglycerol, pentaerythrites, polyols which are obtained by the reduction of carbohydrates (sorbitol, mannitol), monosaccharides, disaccharides, oligosaccharides, polysaccharides, polyvinyl alcohols, and mixtures thereof.

For example, a suitable L unit is a dodecylene unit having the formula:

wherein an equivalent of 1,12-dichlorododecane is reacted, for example, with a suitable amount of a PA unit to produce a polyamine which is crosslinked via dodecylene units. For the purposes of the present invention, L crosslinking units which comprise only carbon and hydrogen are considered to be "hydrocarbyl" L units. Preferred hydrocarbyl units are polyalkylene units have the formula:

wherein n is from 1 to about 50.

Hydrocarbyl L units may be derived from hydrocarbons having two units which are capable of reacting with the nitrogen of the PA units. Non-limiting examples of precursors which result in the formation of hydrocarbyl L units include 1,6-dibromohexane, 1,8-ditosyloctane, and 1,14-dichlorotetradecane.

Further examples of preferred non-amide forming crosslinking L units are the units which derive from crosslinking units wherein epihalohydrin is used as the connecting unit. For example, 1,12-dihydroxydodecane is reacted with epichlorohydrin to form the bis-epoxide non-amide forming L unit precursor having the formula:

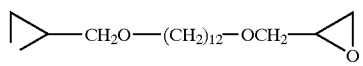

which when reacted with one or more PA units or $(PA)_w(T)_x$ units results in an L crosslinking unit having the formula:

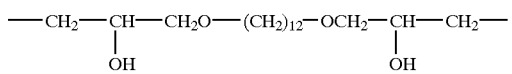

however, it is not necessary to pre-form and isolate the bis-epoxide, instead the crosslinking unit precursor may be formed in situ by reaction of 1,12-dihydroxydodecane or other suitable precursor unit with epihalohydrin in the presence of grafted or ungrafted PA units or $(PA)_w(T)_x$ units.

Other crosslinking L units which utilize one or more epihalohydrin connecting 20 units include polyalkyleneoxy L units having the formula:

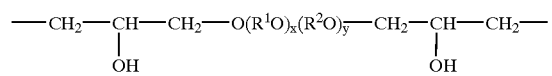

wherein R' is ethylene, $R^2$ is 1,2-propylene, x is from 0 to 100 and y is from 0 to 100. Another preferred unit which can comprise an L unit and which can be suitably combined with epihalohydrin connecting units include polyhydroxy units having the formula:

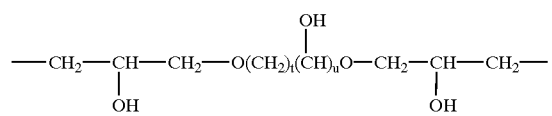

wherein the index t is from at least 2 to about 20 and the index u is from 1 to about 6. The formulator may also combine units to form hybrid L crosslinking units, for example, units having the formula:

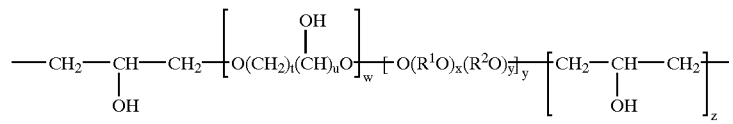

wherein the indices w and y are each independently from 1 to 50, z is units are present in a sufficient to suitably connect the polyhydroxy units and the polyalkyleneoxy units into the backbone without the formation of ether linkages.

The following is an example of an L linking group which comprises both a polyalkyleneoxy and a polyhydroxy unit.

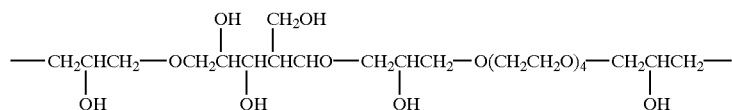

A further example of a preferred crosslinking L units are units which comprises at least two aziridine groups as connecting groups, for example an L unit having the formula:

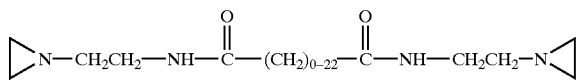

which can be used to link two $(PA)_w$ units, two $(PA)_w(T)_x$ units, or mixtures thereof.

The polyamines of the present invention may have varying final compositions, for example, $(PA)_w(T)_x$, $[(PA)_w(T)_x]_y[L]_z$, $[(PA)]_w[L]_z$, and mixtures thereof, wherein each PA unit may be grafted or ungrafted. The indices w and x have values such that the ratio of w to x is from 0.8:1 to 1.5:1; y and z have values such that said polyamido compound comprises from about 0.05, preferably to about 0.3 to 2 parts by weight of said L unit. In the cases wherein no crosslinking takes place the indices w and y will be equal to 1 and x and z will be equal to 0. In the case wherein no crosslinking occurs using L units, the index y is equal to 1 and z is equal to 0. In the case wherein no crosslinking occurs using T units, the indices w and y are equal to 1 and x is equal to 0.

A preferred embodiment of the present invention which comprises PA units, T units, and L units includes the reaction product of:
  a) 1 part by weight, of a polyamine obtained by condensation of 1 mole of a dicarboxylic acid with a polyalkylene polyamine (i.e., diethylenetriamine) to the extent wherein at least about 10% of the —NH backbone hydrogens are unmodified by reaction with said dicarboxylic acid, then optionally reacting the obtained polyamine condensation product with up to 12 ethyleneimine units (i.e., grafting of the backbone using aziridine) per basic nitrogen atom; and
  b) further reacting the product obtained in (a) with from 0.05, preferably from about 0.3 to about 2 parts by weight, of an L units, inter alia the reaction product of a polyalkylene oxide having from 8 to 100 alkylene oxide units with epichlorohydrin at a temperature of form about 20° C. to about 100° C.

A preferred embodiment of the present invention are the water-soluble condensation products which can be obtained by the reaction of:
  a) polyalkyleneimines and polyalkyleneimines grafted with ethyleneimines, and mixtures thereof; with
  b) at least bifunctional halogen-free cross-linking agents, said agents selected from the group consisting of:
    i) ethylene carbonate, propylene carbonate, urea, and mixtures thereof;
    ii) mono-carboxylic acids comprising one olefin moiety inter alia acrylic acid, methacrylic acid, crotonic acid; and the esters, amides, and anhydrides thereof; polycarboxylic acids inter alia oxalic acid, succinic acid, tartaric acid, itaconic acid, maleic acid; and the esters, amides, and anhydrides thereof;
    iii) reaction products of polyetherdiamines, alkylenediamines, polyalkylene-diamines, and mixtures thereof, with mono-carboxylic acids comprising one olefin moiety wherein the resulting polyamine comprises a functional units which is selected from the group consisting of at least two ethylenically unsaturated double bonds, carbonamide, carboxyl group, ester group, and mixtures thereof;
    iv) at least two aziridine group-containing reaction products of dicarboxylic acid esters with ethyleneimine and mixtures of the cross-linking agents.

However, prior to reaction of $(PA)_w(T)_x$ units formed herein above, the $(PA)_w(T)_x$ polyamine compound may be partially amidated ("capped" as described herein above) by treatment with a mono carboxylic acid or the esters of mono carboxylic acids. The formulator may vary the degree to which the backbone nitrogens are amidated according to the desired properties of the final soil entrainment system. Non-limiting examples of suitable mono-carboxylic acids include formic acid, acetic acid, propionic acid, benzoic acid, salicylic acid, lauric acid, palmitic acid, stearic acid, oleic acid, linoleic acid, behenic acid, and mixtures thereof.

The high molecular weight modified polyamine condensation products of the present invention (also referred to herein as "resins") are preferably formed from the reaction of one or more grafted, cross-linked polyethyleneimines and one or more polyethylene and/or polypropylene glycol copolymers, wherein the resulting crosslinked modified polyamines (resins) have a final viscosity of more than or equal to 300 mPa-sec., preferably from 400 to 2,500 mPa-sec. when measured at 20° C. in a 20% aqueous solution. The modified polyamine compounds of the present invention are suitably described in U.S. Pat. No. 3,642,572 Eadres et al., issued Feb. 15, 1972, U.S. Pat. No. 4,144,123 Scharf et al., issued Mar. 13, 1979 and U.S. Pat. No. 4,371,674 Hertel et al., issued February 1, 1983, NE 6,612,293, DT 1,946,471, DT 36386, DT 733,973, DE 1,771,814, all of which are included herein by reference. Examples of preferred modified polyamine are Lupasol SK and Lupasol SKA avaliable from BASF.

2) Modified Polyacryalminde Polymers—The modified polyacrylamide polymers useful in the present invention have the formula:

wherein each R unit is independently hydrogen, $C_1$–$C_{12}$ alkyl, $C_6$–$C_{12}$ aryl, $CON(R')_2$, and D as described herein below; preferably $C_1$–$C_4$ alkyl, hydrogen, D units and $CON(R')_2$, more preferably hydrogen, D units and $CON(R')_2$, wherein each R' is independently selected from hydrogen, $C_1$–$C_6$ alkyl, or both R' units can be taken together to form a ring comprising 4–6 carbon atoms, preferably hydrogen, $C_1$–$C_6$ alkyl.

For the purposes of the present invention the term "homopolymeric" is defined as "a polymer backbone which is comprised of units having the same unit composition, i.e., formed from polymerization of the same monomer". For the purposes of the present invention the term "copolymeric" is defined as "a polymer backbone which is comprised of units having a different unit composition, i.e., formed from the polymerization of two or more monomers".

The number of D units present in the modified polyacrylamide polymers depends upon the formulation. For example, the number of D units will be adjusted to provide water solubility of the polymer. The molecular weight of the modified polyacrylamide polymers useful in the present invention are from about 20,000 Daltons to about 10,000,000 Daltons, more preferably from about 200,000 Daltons to about 15,000,000 Daltons, even more preferably still from about 350,000 Daltons to about 15,000,000 Daltons. Therefore the value of the index n is selected to provide the indicated molecular weight, and providing for a water solubility of least 100 ppm, preferably at least about 300 ppm, and more preferably at least about 1,000 ppm in water at ambient temperature which is defined herein as 25° C.

Each D is independently selected from the group consisting of, $CO_2N(R')_m$, $CON(R')CH_2CON(R')_2$, $OCON(R')_2$, $CO_2(CH_2)_qN(R')_m$, preferably $CO_2(CH_2)_qN(R')_m$, $CO_2N(R')_m$; wherein R' is as defined above, q is an integer from 0 to 5, preferably from 0 to 3, more preferably from 0 to 2, and m is either 2 or 3. One preferred D is the quaternary N substituted acrylamides, such as $CO_2(CH_2)_qN^+(R')_3$.

The indices m and n, when present, are such that the molecular weight of said polyamines is from about 20,000 Daltons to about 10,000,000 Daltons, more preferably from about 200,000 Daltons to about 15,000,000 Daltons, even more preferably still from about 350,000 Daltons to about 15,000,000 Daltons.

Depending upon the selection of R, D and R' the modified polacrylamide polymers each subsituents can be charge or neutral, with netral or cationally charged being prefered. In one preferred embodiment at least 50%, more preferably at least 60%, even more preferably at least 75% of the substituents of the modified polacrylamide polymers have a cationic charge.

Suitable modified polyacrylamide polymers include the Sedipur range of polyacrylamide polymers avaliable from BASF. The most preferred are the Sedipur C types, which are cationic substituted polyarcylamides, such as Sedipur CF 803.

3) Polyethylene Glycols (a.k.a. Polyethylene oxide, or PEG)—The polyethylene glycols, or PEG's suitable for use in the present invention have an average molecular weight of from about 400,000 daltons to about 15,000,000 daltons, more preferably from about 800,000 daltons to about 15,000,000 daltons, even more preferably from about 1,500,000 daltons to about 15,000,000 daltons.

More information about PEG's and methods of synthesis can be found in "Polyethers (ethylene oxide polymers)" Kirk Othmer's Encyclopedia of Chemical Technology, 4th Edition, Wiley, N.Y., 1991.

Adjunct Ingredients

The compositions of the present invention further comprise an adjunct ingredient. Typically this adjunct ingredient is selected from the group consisting of surfactants, buffers, solvent, enzymes, perfume, suds suppressor, antimicrobial agents, and mixtures thereof.

The adjunct ingredient will be present in varying amounts depending either upon their function in the cleaning composition or desired concentration in solution or on the surface to be cleaned. Furthermore, it is preferred to use adjunct ingredients which are compatible with the soil entrainment system and cause an insignificant, or no streaking or hazing on the cleaned surface upon drying.

Typically, the adjunct ingredient will be present in an effective amount, preferably from about 0.0001% to about 99.9%, more preferably from about 0.0005% to about 99.9%, by weight of composition.

Surfactant—Typically, when present the surfactant will be selected from those which are typically used in hard surface cleaning. When present the surfactant is preferably selected from the group consisting of anionic, nonionic, zwitterionic, amphoteric and mixtures thereof.

The compositions of the present invention may optionally contain one or more detergent surfactants. It is preferred that these surfactants are selected from the group consisting of anionic, nonionic, zwitterionic, cationic, amphoteric and mixtures thereof, more preferably the detergent surfactant has a linear or branched structure and is selected from the group consisting of anionic and nonionic detergent surfactants. Even more preferably anionic and nonionic detergent surfactants having hydrophobic chains containing from about 8 to about 18, preferably from about 8 to about 15, carbon atoms. Examples of anionic surfactants include, but are not limited to, linear alkyl sulfates, alkyl sulfonates, and the like. Examples of nonionic surfactants include alkylethoxylates and the like. Examples of zwitterionic surfactants include betaines and sulfobetaines. Examples of amphoteric surfactants include alkylampho glycinates, and alkyl imino propionate. Further example of suitable surfactants are described in McCutcheon's Vol. 1: Emulsifiers and Detergents, North American Ed., McCutheon Division, MC Publishing Co., 1995, which is incorporated herein by reference.

Suitable anionic surfactants typically comprise a hydrophobic chain containing from about 8 carbon atoms to about 18, preferably from about 8 to about 16, carbon atoms, and typically include a sulfonate or carboxylate hydrophilic head group.

Suitable anionic surfactants include the $C_8$–$C_{18}$ alkyl sulfonates, $C_{10}$–$C_{14}$ linear or branched alkyl benzene sulfonates, $C_{10-14}$ alkyl sulfates and ethoxysulfates (e.g., Stepanol AM® from Stepan)., $C_9$–$C_{15}$ alkyl ethoxy carboxylates (Neodox® surfactants available from Shell Chemical Corporation),. Suitable commercially available sulfonates are available from Stepan under the tradename Bio-Terge PAS-8® as well as from the Witco Corporation under the tradename Witconate NAS-8®, and Hostapur SAS® from Hoechst, Aktiengesellschaft, D-6230 Frankfurt, Germany.

One type of prefered nonionic surfactant are the alkylpolysaccharides that are disclosed in U.S. Pat. Nos.: 5,776,872, Cleansing compositions, issued Jul. 7, 1998, to Giret, Michel Joseph; Langlois, Anne; and Duke, Roland Philip; 5,883,059, Three in one ultra mild lathering antibacterial liquid personal cleansing composition, issued Mar. 16, 1999, to Furman, Christopher Allen; Giret, Michel Joseph; and Dunbar, James Charles; etc.; 5,883,062, Manual dishwashing compositions, issued Mar. 16, 1999, to Addison, Michael Crombie; Foley, Peter Robert; and Allsebrook, Andrew Micheal; and 5,906,973, issued May 25, 1999, Process for cleaning vertical or inclined hard surfaces, by Ouzounis, Dimitrios and Nierhaus, Wolfgang.

Suitable alkylpolysaccharides for use herein are disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group. For acidic or alkaline cleaning compositions/solutions suitable for use in no-rinse methods, the preferred alkyl polysaccharide preferably comprises a broad distribution of chain lengths, as these provide the best combination of wetting, cleaning, and low residue upon drying. This "broad distribution" is defined by at least about 50% of the chainlength mixture comprising from about 10 carbon atoms to about 16 carbon atoms. Preferably, the alkyl group of the alkyl polysaccharide consists of a mixtures of chainlength, preferably from about 6 to about 18 carbon atoms, more preferably from about 8 to about 16 carbon atoms, and hydrophilic group containing from about one to about 1.5 saccharide, preferably glucoside, groups per molecule. This "broad chainlength distribution" is defined by at least about 50% of the chainlength mixture comprising from about 10 carbon atoms to about 16 carbon atoms. A broad mixture of chain lengths, particularly $C_8$–$C_{16}$, is highly desirable relative to narrower range chain length mixtures, and particularly versus lower (i.e., $C_8$–$C_{10}$ or $C_8$–$C_{12}$) chainlength alkyl polyglucoside mixtures. It is also found that the preferred $C_{8-16}$ alkyl polyglucoside provides much improved perfume solubility versus lower and narrower chainlength alkyl polyglucosides, as well as other preferred surfactants, including the $C_8$–$C_{14}$ alkyl ethoxylates. Any reducing saccharide containing 5 or 6 carbon atoms can be used, e.g., glucose, galactose and galactosyl moieties can be substituted for the glucosyl moieties. (optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units. The glycosyl is preferably derived from glucose.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from 8 to 18, preferably from 10 to 16, carbon atoms. Preferably, the alkyl group is a straight-chain saturated alkyl group. The alkyl group can contain up to about 3 hydroxyl groups and/or the polyalkyleneoxide chain can contain up to about 10, preferably less than 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides and/or galatoses. Suitable mixtures include coconut alkyl, di-, tri-, tetra-, and pentaglucosides and tallow alkyl tetra-, penta- and hexaglucosides.

To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-,3-, 4- and/or 6-position, preferably predominantly the 2-position.

In the alkyl polyglycosides, the alkyl moieties can be derived from the usual sources like fats, oils or chemically produced alcohols while their sugar moieties are created from hydrolyzed polysaccharides. Alkyl polyglycosides are the condensation product of fatty alcohol and sugars like glucose with the number of glucose units defining the relative hydrophilicity. As discussed above, the sugar units can additionally be alkoxylated either before or after reaction with the fatty alcohols. Such alkyl polyglycosides are described in detail in WO 86/05199 for example. Technical alkyl polyglycosides are generally not molecularly uniform products, but represent mixtures of alkyl groups and mixtures of monosaccharides and different oligosaccharides. Alkyl polyglycosides (also sometimes referred to as "APG's") are preferred for the purposes of the invention since they provide additional improvement in surface appearance relative to other surfactants. The glycoside moieties are preferably glucose moieties. The alkyl substituent is preferably a saturated or unsaturated alkyl moiety containing from about 8 to about 18 carbon atoms, preferably from about 8 to about 10 carbon atoms or a mixture of such alkyl moieties. $C_8$–$C_{16}$ alkyl polyglucosides are commercially available, Simusol® surfactants from Seppic Corporation, 75 Quai d'Orsay, 75321 Paris, Cedex 7, France, and Glucopon®425 available from Henkel. However, it has been found that purity of the alkyl polyglucoside can also impact performance, particularly end result for certain applications, including daily shower product technology. In the present invention, the preferred alkyl polyglucosides are those which have been purified enough for use in personal cleansing. Most preferred are "cosmetic grade" alkyl polyglucosides, particularly $C_8$ to $C_{16}$ alkyl polyglucosides, such as Plantaren 2000®, Plantaren 2000 N®, and Plantaren 2000 N UP®, available from Henkel Corporation (Postfach 101100, D 40191 Dusseldorf, Germany).

Another class of preferred nonionic surfactant is alkyl ethoxylates. The alkyl ethoxylates of the present invention are either linear or branched, and contain from about 8 carbon atoms to about 14 carbon atoms, and from about 4 ethylene oxide units to about 25 ethylene oxide units. Examples of alkyl ethoxylates include Neodol® 91-6, Neodol 91-8® supplied by the Shell Corporation (P.O. Box 2463, 1 Shell Plaza, Houston, Tex.), and Alfonic® 810-60 supplied by Vista corporation, (900 Threadneedle P.O. Box 19029, Houston, Tex.). More preferred surfactants are the alkyl ethoxylates comprising from about 9 to about 12 carbon atoms, and from about 4 to about 8 ethylene oxide units. These surfactants offer excellent cleaning benefits and work synergistically with the required hydrophilic polymers. A most preferred alkyl ethoxylate is $C_{11}EO_5$, available from the Shell Chemical Company under the trademark Neodol® 1-5.

Alternative nonionic detergent surfactants for use herein are alkoxylated alcohols generally comprising from about 6 to about 16 carbon atoms in the hydrophobic alkyl chain of the alcohol. Typical alkoxylation groups are propoxy groups or propoxy groups in combination with ethoxy groups. Such compounds are commercially available under the tradename Antarox® available from Rhodia (CN 7500, Cranberry, N.J.). with a wide variety of chain length and alkoxylation degrees. Block copolymers of ethylene oxide and propylene oxide can also be used and are available from BASF under the tradename Pluronic®. Preferred nonionic detergent surfactants for use herein are according to the formula $R(X)_nH$, were R is an alkyl chain having from about 6 to about 16 carbon atoms, preferably from about 8 to about 12, X is a propoxy, or a mixture of ethoxy and propoxy groups, n is an integer of from about 4 to about 30, preferably from about 5 to about 8. Other non-ionic surfactants that can be used include those derived from natural sources such as sugars and include $C_8$–$C_{16}$ N-alkyl glucose amide surfactants.

Also so suitable for use in the present invention are the fluorinated nonionic surfactants. One particularly suitable fluorinated nonionic surfactant is Fluorad F170 (3M). Fluorad F170 has the formula:

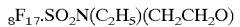

$_8F_{17}.SO_2N(C_2H_5)(CH_2CH_2O)$

Also suitable for use in the present invention are silicone containing surfactants. One example of these types of surfactants is Silwet L7604 avaliable from Union Carbide.

Some preferred commercially available surfactants include Neodol 11-5, Nonidet SF-3, Nonidet SF-5, (all Shell Chemical), C8 sulfonate (Witconate NA-8) C11–18 APG (Henkel), Fluorad F170 (3M).

In general, the level of optional surfactants, when present in the compositions herein is from about 0% to about 0.25%, more preferably from about 0.001% to about 0.2%, even more preferably from about 0.01% to about 0.15%, by weight of the composition.

Buffer—The buffering agent may be an active detergent in its own right, or it may be a low molecular weight, organic or inorganic material that is used in this composition solely for maintaining the desired pH. The buffer can be alkaline, acidic or neutral. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are Tri (hydroxymethyl)amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl)methyl glycine (tricine). Other suitable buffers include ammonium carbamate, citric acid, acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see McCutcheon's EMULSIFIERS AND DETERGENTS, North American Edition, 1997, McCutcheon Division, MC Publishing Company Kirk and WO 95/07971 both of which are incorporated herein by reference.

Preferred buffers include, but are not limited to, ammonia, methanol amine, ethanol amine, 2-amino-2-methyl-1-propanol, 2-dimethylamino-2-methyl-1-propanol, 1,3-bis (methylamine)-cyclohexane, acetic acid, glycolic acid and the like. Most preferred among these are ammonia, 1,3-bis (methylamine)-cyclohexane, 2-dimethylamino-2-methyl-1-propanol and acetic acid.

In one preferred aspect the composition of the present invention wherein to minimize streaking/filming problems, the buffering is provided, at least in part, by volatile materials whose molecular weight is less than about 400 g/mole.

The composition will preferably contain at least about 0%, more preferably at least about 0.001%, even more preferably still, at least about 0.01% by weight of the composition of buffering agent. The composition will also preferably contain no more than about 1%, more preferably no more than about 0.75%, even more preferably, no more than about 0.5% by weight of the composition of buffering agent.

Aqueous liquid carrier—The compositions of the present invention may also contain an aqueous liquid carrier, preferably from about 10% to about 99.9%, preferably from about 30% to about 98%, by weight the composition. The most preferred of which is water.

It is preferred that any water in the composition, such as in premixed or ready to use solutions, is deionized or softened water. However, conventional tap water can be used.

Solvent—The compositions, optionally, can also contain one, or more, solvents at effective levels, typically, when present, no less than about 0.25%, and, at least about, in increasing order of preference, about 0.5% and about 3.0%, and no more than about, in increasing order of preference, about 7% and about 5% by weight of the composition.

The surfactant provides cleaning and/or wetting even without a cleaning solvent present. However, the cleaning can normally be further improved by the use of the right solvent. By solvent, it is meant an agent which assists the surfactant to remove soils such as those commonly encountered in the home. The solvent also can participate in the building of viscosity, if needed, and in increasing the stability of the composition.

Such solvents typically have a terminal $C_3$–$C_6$ hydrocarbon attached to from one to three ethylene glycol or propylene glycol moieties to provide the appropriate degree of hydrophobicity and, preferably, surface activity. Examples of commercially available hydrophobic cleaning solvents based on ethylene glycol chemistry include mono-ethylene glycol n-hexyl ether (Hexyl Cellosolve® available from Union Carbide). Examples of commercially available hydrophobic cleaning solvents based on propylene glycol chemistry include the di-, and tri-propylene glycol derivatives of propyl and butyl alcohol, which are available from Arco Chemical, 3801 West Chester Pike, Newtown Square, Pa. 19073) and Dow Chemical (1691 N. Swede Road, Midland, Mich.) under the trade names Arcosolv® and Dowanol®.

In the context of the present invention, preferred solvents are selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, methanol, ethanol, isopropanol, n-butanol, iso-butanol, pentanol, 2-methyl-1-butanol, 2-butanone, methoxymethanol, methoxyethanol, methoxy propanol, ethoxypropanol, propoxypropanol, ethoxybutanol and mixtures thereof. "Butyl" includes both normal butyl, isobutyl and tertiary butyl groups. More prefered solvents include ethanol, propanol, propoxypropanol, mono-propylene glycol and mono-propylene glycol mono-butyl ether. The latter two are available under the tradenames Dowanol DPnP® and Dowanol DPnB®. Di-propylene glycol mono-t-butyl ether is commercially available from Arco Chemical under the tradename Arcosolv PTB®.

The amount of solvent can vary depending on the amount of other ingredients present in the composition. The solvent is normally helpful in providing good cleaning, such as in floor cleaner applications.

Perfumes—Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual perfumery ingredients can comprise from about 0.0001% to about 90% of a finished perfume composition.

When present the perfume comprises from about 0% to about 0.5%, more preferably from about 0.001% to about 0.1%, even more preferably still 0.005% to about 0.08%, by weight of the composition.

Antimicrobial Agents—The compositions, optionally, can also contain one, or more, antimicrobial agents. The antimicrobial agents are selected from those typically used in hard surface cleaning with the proviso that they are compatible with the soil entrainment system and cause an insignificant, or no streaking or hazing on the cleaned surface upon drying. Suitable antimicrobial agents include Quaternary amines, such as Didecyldimethylammonium chloride (Bardac 2250, Lonza); chlorhexidine digluconate, methylbenzethonium chloride, Dodecyltriphenyphosphonium bromide and mixtures thereof.

When present the antimicrobial agents comprises from about 0% to about 0.5%, more preferably from about 0.0001% to about 0.25%, even more preferably still 0.001% to about 0.1%, by weight of the composition.

Suds Suppressor—The composition of the present invention can optionally contain a suds suppressor. When present the suds suppressor is preferably present from about 0.0005% to about 0.01%, more preferably from about 0.001% to about 0.005%, by weight of the composition.

Suitable suds suppressors include, silicone suds suppressor such as silicone polymers and linear or branched $C_{10}$–$C_{18}$ fatty acids or alcohols, with silicone suds suppressor being preferred. One suitable suds supressor is Dow Coming silicone SS Another suitable suds suppressors is a mixture of Polyethylene glycol stearate (4% Wt, CAS #9004993); Methylated silica (2% Wt, CAS #67762907); Octamethyl cyclotetrasiloxane (2% Wt, CAS #556672), avaliable from Dow Corning.

Further examples of suitable suds suppressors can be found in co-pending U.S. patent applications Ser. Nos. 60/041,273, filed Mar. 20, 1997 by R. A. Masters, et al. (P&G Case 6555P), and 60/045,858, filed May 8, 1997 by R. A. Masters, et al. (P&G Case 6555P2), both of which are incorporated by reference herein.

Corrosion Inhibitor—The composition of the present invention may optionally contain a corrosion inhibitor. When present the corrosion inhibitor is preferably present from about 0.0001% to about 0.2%, preferably from about 0.0001% to about 0.1%, more preferably from about 0.0005% to about 0.08% by weight of the composition.

While not wishing to be limited by theory, it is believed that the functional role of the corrosion inhibitor is to form 'in use' a protective coating layer on any metal components of an implement in which the compositions of the invention are being stored and applied to a hard surface through. Furthermore, the corrosion inhibitor have the additional benefit of providing corrosion inhibition to the surfaces to which it is applied. Such surfaces would include ranges, refrigerators, and any other surface which is wetted in delivering the solution to the hard surface, such as the floor.

It is preferred that the corrosion inhibitor, when present in the composition is selected from the group consisting of alkali metal or alkaline earth salts of silicate (such as layered sodium silicate e.g. $\delta$-$Na_2Si_2O_5$, known as NaSKS-6 (trade name), available from Hoechst AG), alkali metal or alkaline earth salts of metasilicate, polyvalent ion salts of fatty acids, alkyl phosphates, paraffin, benzotriazole, inorganic salts of $Bi^{2+}$, organosilicates, inorganic salts of $Zn^{2+}$, and mixtures thereof. It is also preferable to minimize the amount of chloride ions present in the composition as higher levels of chloride ions are believed to increase corrosion.

Suitable corrosion inhibitors can also be found in U.S. Pat. No. 4,199,483; U.S. Pat. No. 4,992,195; U.S. Pat. No. 4,098,720; U.S. Pat. No. 5,736,495; U.S. Pat. No. 3,981,780; U.S. Pat. No. 4,292,190; all of which are hereby incorporated by reference.

Other Optional Composition Ingredients—The composition, herein, may further comprise other optional ingredients. Suitable ingredients include, but not limited to: detergent builders, dyes, enzymes, leveling agents, chelating agents, thickening agents, stabilizers, antioxidants, etc.

Suitable detergent builders include those derived from phosphorous sources, such as orthophosphates, pyrophosphates, tripolyphosphates, etc., and those derived from non-phosphorous sources, such as nitrilotriacetates; and the like. Suitable enzymes include lipases, proteases, amylases and other enzymes known to be useful for catalysis of soil degradation. Suitable leveling agents include polysaccharide gum, such as guar gum, Xanthum gum, etc.

The total level of such optional ingredients is low, preferably less than about 0.01%, more preferably less than about 0.05%, to avoid causing hazing or ilming/streaking problems. It is preferred that any water in the composition, such as in premixed or ready to use solutions, is deionized or softened water.

Cleaning Kits

In another aspect of the present invention a kit is provided for. This kit can have an assembly of one or more units, either packaged together or separately. For example, the kit can include a pad or a dry wipe with cleaning solution. A second example is a kit with pad or dry wipe, implement and solution. A third example is a kit with concentrated refill, ready to use solution and pads with superabsorbent gelling. This kit comprises an implement containing a pad containing superabsorbent material and a detergent composition that provides effective cleaning and good particulate soil removal when used with a disposable cleaning pad and without rinsing comprising an effective amount of an soil entrainment system.

It is preferred that the implement comprises:
a. a handle; and
b. a removable cleaning pad preferably containing an effective amount of a superabsorbent material, and having a plurality of substantially planar surfaces, wherein each of the substantially planar surfaces contacts the surface being cleaned, more preferably said pad is a removable cleaning pad having a length and a width, the pad comprising
  i. a scrubbing layer; and
  ii. an absorbent layer comprising a first layer and a second layer, where the first layer is located between the scrubbing layer and the second layer (i.e., the first layer is below the second layer) and has a smaller width than the second layer.

An important aspect of the cleaning performance provided by the preferred pad is related to the ability to provide multiple planar surfaces that contact the soiled surface during the cleaning operation. In the context of a cleaning implement such as a mop, these planar surfaces are provided such that during the typical cleaning operation (i.e., where the implement is moved back and forth in a direction substantially perpendicular to the pad's width), each of the planar surfaces contact the surface being cleaned as a result of "rocking" of the cleaning pad.

In one preferred aspect of the present invention, the kit further contains instructions for use of the kit which are in association with the composition and the implement to insure optimum usage. In a further preferment of this aspect, these instructions are on the back of the pad in the form of words and/or pictures and explain which side of the pad to attach to the implement.

In one preferred aspect of the implement the pad is detachably mounted on the implement. That is, the pad can be removed and replaced by another pad. This is especially useful, when the pad is excessively soiled. The pad can be removed and replaced with a fresh clean pad.

In another preferred aspect the implement further comprises a dosing device. The dosing device delivers the detergent composition to the surface to be cleaned. This dosing device can be battery powered, electrically powered, or hand powered(that is the user works the dosing device, such as a pump manually). It is more preferred that the dosing device be battery or electrically powered and includes a dispensing trigger or button. It is even more preferred that when the dosing device is battery or electrically powered, it applies a continuous flow to the surface to be cleaned.

In another preferred aspect the implement further comprises a reservoir which holds the cleaning solution. It is preferred that, when present, the reservoir is detachably mounted on the implement. It is even more preferred that when implement comprises a detachably mounted reservoir that the implement also comprises a dosing device, even more preferably a battery or electrically powered dosing device.

In one preferred aspect the pad comprises an inner absorbent core with super-absorbent polymer and outer scrub layer made of an apertured form film.

One of ordinary skill in the art can select various materials that can be utilized to prepare the disposable pads and/or implements herein. Thus, while preferred materials are described herein for the various implement and cleaning pad components, it is recognized that the scope of operable materials is not limited to such disclosures.

More details on suitable cleaning pads (such as those which include superabsorbent material), implements, and the components of the implements, such as the removable cleaning pad, handle etc., can be found in co-pending U.S. patent applications Ser. Nos. 08/756,774, filed Nov. 26, 1996 by V. S. Ping, et al. (P&G Case 6383), and 08/716,755, filed Sep. 23, 1996 by A. J. Irwin (P&G Case 6262), 60/061,296, filed Oct. 7, 1997 by N. J. Policicchio, et al. (P&G Case 6873P), 09/037,379, filed Mar. 10, 1998 by R. A. Masters, et al. (P&G Case 6553), 60/041,273, filed Mar. 20, 1997 by R. A. Masters, et al. (P&G Case 6555P), 60/045,858, filed May 8, 1997 by R. A. Masters, et al. (P&G Case 6555P2), 60/085,837, filed May 18, 1998 (P&G Case 7159P), 08/756,999, filed Nov. 26, 1996 (P&G Case 6269R), 08/756,864, filed Nov. 26, 1996 (P&G Case 6270R), 08/756,616, filed Nov. 26, 1996 (P&G Case 6382), 08/756,774, filed Nov. 26, 1996 (P&G Case 6383), 08/756,151, filed Nov. 26, 1996 (P&G Case 6384), 08/756,997, filed Nov. 26, 1996 (P&G Case 6385), 08/756,998, filed Nov. 26, 1996 (P&G Case 6386), 08/756,507, filed Nov. 26, 1996 (P&G Case 6387), 09/188,604, filed Nov. 9, 1998 (P&G Case 7337), 60/110,356, filed Dec. 1, 1998 K. W. Willman, et al. (P&G Case 7367P), 60/110,476, filed Dec. 1, 1998 N. J. Policicchio, et al. (P&G Case 7368P), 09/201,620 filed Nov. 30, 1998, accepted May 25, 1999 (P&G Case 7362), and 09/290,960, filed Apr. 13, 1999 (P&G Case 7497), all of which are incorporated herein by reference. More specific details on implements, and the components of the implements, such as the removable cleaning pad, handle etc., can be found in co-pending U.S. design patent applications Ser. Nos. 29/097,135, filed Nov. 30, 1998 (P&G Case D605), 29/097,132, filed Nov. 30, 1998 (P&G Case D603), and 29/097,585, filed Dec. 12, 1998 (P&G Case D610), all of which are incorporated herein by reference. See also WO Applications Nos. 98/11813, and 98/42819, both of which are incorporated herein by reference.

Cleaning Pad—The cleaning pads will preferably have an absorbent capacity, when measured under a confining pressure of 0.09 psi after 20 minutes (1200 seconds) (hereafter referred to as "$t_{1200}$ absorbent capacity"), of at least about 10 g deionized water per g of the cleaning pad. The absorbent capacity of the pad is measured at 20 minutes (1200 seconds) after exposure to deionized water, as this represents a typical time for the consumer to clean a hard surface such as a floor. The confining pressure represents typical pressures exerted on the pad during the cleaning process. As such, the cleaning pad should be capable of absorbing significant amounts of the cleaning solution within this 1200 second period under 0.09 psi. The cleaning pad will preferably have a $t_{1200}$ absorbent capacity of at least about 15 g/g, more preferably at least about 20 g/g, still more preferably at least about 25 g/g and most preferably at least about 30 g/g. The cleaning pad will preferably have a $t_{900}$ absorbent capacity of at least about 10 g/g, more preferably a $t_{900}$ absorbent capacity of at least about 20 g/g.

Values for $t_{1200}$ and $t_{900}$ absorbent capacity are measured by the performance under pressure (referred to herein as "PUP") method, which is described in detail in the Test Methods section in allowed application Ser. No. 08/756,507, Holt, Masters, and Ping, filed Nov. 26, 1996, said application being incorporated herein, in its entirety, by reference. The application contains a more complete disclosure of the pads, instruments, etc. that are of use herein.

The cleaning pads will also preferably, but not necessarily, have a total fluid capacity (of deionized water) of at least about 100 g, more preferably at least about 200 g, still more preferably at least about 300 g and most preferably at least about 400 g. While pads having a total fluid capacity less than 100 g are within the scope of the invention, they are not as well suited for cleaning large areas, such as seen in a typical household, as are higher capacity pads.

In the pads there is preferably an absorbent layer which serves to retain any fluid and soil absorbed by the cleaning pad during use. While the preferred scrubbing layer, described hereinafter, has some effect on the pad's ability to absorb fluid, the preferred absorbent layer plays a major role in achieving the desired overall absorbency. Furthermore, the absorbent layer preferably comprises multiple layers which are designed to provide the cleaning pad with multiple planar surfaces.

From the essential fluid absorbency perspective, the absorbent layer is preferably capable of removing fluid and soil from any "scrubbing layer" so that the scrubbing layer will have capacity to continually remove soil from the surface. The absorbent layer also is preferably capable of retaining absorbed material under typical in-use pressures to avoid "squeeze-out" of absorbed soil, cleaning solution, etc.

The absorbent layer can comprise any material that is capable of absorbing and retaining fluid during use. To achieve desired total fluid capacities, it will be preferred to include in the absorbent layer a material having a relatively high fluid capacity (in terms of grams of fluid per gram of absorbent material). As used herein, the term "superabsorbent material" means any absorbent material having a g/g capacity for water of at least about 15 g/g, when measured under a confining pressure of 0.3 psi. Because a majority of the cleaning fluids useful with the present invention are aqueous based, it is preferred that the superabsorbent materials have a relatively high g/g capacity for water or water-based fluids.

Representative superabsorbent materials include water insoluble, water-swellable superabsorbent gelling polymers (referred to herein as "superabsorbent gelling polymers") which are well known in the literature. These materials demonstrate very high absorbent capacities for water. The superabsorbent gelling polymers useful in the present invention can have a size, shape and/or morphology varying over a wide range. These polymers can be in the form of particles that do not have a large ratio of greatest dimension to smallest dimension (e.g., granules, flakes, pulverulents, interparticle aggregates, interparticle crosslinked aggregates, and the like) or they can be in the form of fibers, sheets, films, foams, laminates, and the like. The use of superabsorbent gelling polymers in fibrous form provides the benefit of providing enhanced retention of the superabsorbent material, relative to particles, during the cleaning process. While their capacity is generally lower for aqueous-based mixtures, these materials still demonstrate significant absorbent capacity for such mixtures. The patent literature is replete with disclosures of water-swellable materials. See, for example, U.S. Pat. No. 3,699,103 (Harper et al.), issued Jun. 13, 1972; U.S. Pat. No. 3,770,731 (Harmon), issued Jun. 20, 1972; U.S. Reissue Patent 32,649 (Brandt et al.), reissued Apr. 19, 1989; U.S. Pat. No. 4,834,735 (Alemany et al.), issued May 30, 1989.

Superabsorbent gelling polymers useful in the present invention include a variety of water-insoluble, but water-swellable polymers capable of absorbing large quantities of fluids. Such polymeric materials are also commonly referred to as "hydrocolloids", and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholine, and N,N-dimethylaminoethyl or N,N-diethylaminopropyl acrylates and methacrylates, and the respective quaternary salts thereof. Well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Preferred superabsorbent gelling polymers contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478, all of said patents being incorporated by reference.

Most preferred polymer materials for use in making the superabsorbent gelling polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e. poly (sodium acrylate/acrylic acid)). Network crosslinking renders the polymer substantially water-insoluble and, in part, determines the absorptive capacity and extractable polymer content characteristics of the superabsorbent gelling polymers. Processes for network crosslinking these polymers and typical network crosslinking agents are described in greater detail in U.S. Pat. No. 4,076,663.

While the superabsorbent gelling polymers is preferably of one type (i.e., homogeneous), mixtures of polymers can also be used in the implements of the present invention. For example, mixtures of starch-acrylic acid graft copolymers and slightly network crosslinked polymers of partially neutralized polyacrylic acid can be used in the present invention.

While any of the superabsorbent gelling polymers described in the prior art can be useful in the present invention, where significant levels (e.g., more than about 50% by weight of the absorbent structure) of superabsorbent gelling polymers are to be included in an absorbent structure, and in particular where one or more regions of the absorbent layer will comprise more than about 50%, by weight of the region, the problem of gel blocking by the swollen particles can impede fluid flow and thereby adversely affect the ability of the gelling polymers to absorb to their full capacity in the desired period of time. U.S. Pat. No. 5,147,343 (Kellenberger et al.), issued Sep. 15, 1992 and U.S. Pat. No. 5,149,335 (Kellenberger et al.), issued Sep. 22, 1992, describe superabsorbent gelling polymers in terms of their Absorbency Under Load (AUL), where gelling polymers absorb fluid (0.9% saline) under a confining pressure of 0.3 psi. (The disclosure of each of these patents is incorporated herein by reference.) The methods for determining AUL are described in these patents. Polymers described therein can be particularly useful in embodiments of the present invention that contain regions of relatively high levels of superabsorbent gelling polymers. In particular, where high concentrations of superabsorbent gelling polymer are incorporated in the cleaning pad, those polymers will preferably have an AUL, measured according to the methods described in U.S. Pat. No. 5,147,343, of at least about 24 ml/g, more preferably at least about 27 ml/g after 1 hour; or an AUL, measured according to the methods described in U.S. Pat. No. 5,149,335, of at least about 15 ml/g, more preferably at least about 18 ml/g after 15 minutes. Commonly assigned U.S. application Ser. Nos. 08/219,547 (Goldman et al.), filed Mar. 29, 1994 and 08/416,396 (Goldman et al.), filed Apr. 6, 1995 (both of which are incorporated by reference herein), also address the problem of gel blocking and describe superabsorbent gelling polymers useful in overcoming this phenomena. These applications specifically describe superabsorbent gelling polymers which avoid gel blocking at even higher confining pressures, specifically 0.7 psi. In the embodiments of the present invention where the absorbent layer will contain regions comprising high levels (e.g., more than about 50% by weight of the region) of superabsorbent gelling polymer, it can be preferred that the superabsorbent gelling polymer be as described in the aforementioned applications by Goldman et al.

Other useful superabsorbent materials include hydrophilic polymeric foams, such as those described in commonly assigned U.S. patent application Ser. No. 08/563,866 (DesMarais et al.), filed Nov. 29, 1995 and U.S. Pat. No. 5,387,207 (Dyer et al.), issued Feb. 7, 1995. These references describe polymeric, hydrophilic absorbent foams that are obtained by polymerizing a high internal phase water-in-oil emulsion (commonly referred to as HIPEs). These foams are readily tailored to provide varying physical properties (pore size, capillary suction, density, etc.) that affect fluid handling ability. As such, these materials are particularly useful, either alone or in combination with other such foams or with fibrous structures, in providing the overall capacity required by the present invention.

Where superabsorbent material is included in the absorbent layer, the absorbent layer will preferably comprise at least about 15%, by weight of the absorbent layer, more preferably at least about 20%, still more preferably at least about 25%, of the superabsorbent material.

The absorbent layer can also consist of or comprise fibrous material. Fibers useful in the present invention include those that are naturally occurring (modified or unmodified), as well as synthetically made fibers. Examples of suitable unmodified/modified naturally occurring fibers include cotton, Esparto grass, bagasse, hemp, flax, silk, wool, wood pulp, chemically modified wood pulp, jute, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, Rayon®, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The absorbent layer can comprise solely naturally occurring fibers, solely synthetic fibers, or any compatible combination of naturally occurring and synthetic fibers.

The fibers useful herein can be hydrophilic, hydrophobic or can be a combination of both hydrophilic and hydrophobic fibers. As indicated above, the particular selection of hydrophilic or hydrophobic fibers depends upon the other materials included in the absorbent (and to some degree the scrubbing) layer. That is, the nature of the fibers will be such that the cleaning pad exhibits the necessary fluid delay and overall fluid absorbency. Suitable hydrophilic fibers for use in the present invention include cellulosic fibers, modified cellulosic fibers, rayon, polyester fibers such as hydrophilic nylon (HYDROFIL®). Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemi-thermomechanical pulp processes. Recycled or secondary wood pulp fibers, as well as bleached and unbleached wood pulp fibers, can be used.

Another type of hydrophilic fiber for use in the present invention is chemically stiffened cellulosic fibers. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Where fibers are used as the absorbent layer (or a constituent component thereof), the fibers can optionally be combined with a thermoplastic material. Upon melting, at least a portion of this thermoplastic material migrates to the intersections of the fibers, typically due to interfiber capillary gradients. These intersections become bond sites for the thermoplastic material. When cooled, the thermoplastic materials at these intersections solidify to form the bond sites that hold the matrix or web of fibers together in each of the respective layers. This can be beneficial in providing additional overall integrity to the cleaning pad.

Amongst its various effects, bonding at the fiber intersections increases the overall compressive modulus and strength of the resulting thermally bonded member. In the case of the chemically stiffened cellulosic fibers, the melting and migration of the thermoplastic material also has the effect of increasing the average pore size of the resultant web, while maintaining the density and basis weight of the web as originally formed. This can improve the fluid acquisition properties of the thermally bonded web upon initial exposure to fluid, due to improved fluid permeability, and upon subsequent exposure, due to the combined ability of the stiffened fibers to retain their stiffness upon wetting and the ability of the thermoplastic material to remain bonded at the fiber intersections upon wetting and upon wet compression. In net, thermally bonded webs of stiffened fibers retain their original overall volume, but with the volumetric regions previously occupied by the thermoplastic material becoming open to thus increase the average interfiber capillary pore size.

Thermoplastic materials useful in the present invention can be in any of a variety of forms including particulates, fibers, or combinations of particulates and fibers. Thermoplastic fibers are a particularly preferred form because of their ability to form numerous interfiber bond sites. Suitable thermoplastic materials can be made from any thermoplastic polymer that can be melted at temperatures that will not extensively damage the fibers that comprise the primary web or matrix of each layer. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in the cleaning pads, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. Depending upon the desired characteristics for the resulting thermally bonded absorbent member, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., those available from Danaklon a/s, Chisso Corp., and CELBOND®, available from Hercules). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses.

Methods for preparing thermally bonded fibrous materials are described in U.S. application Ser. No. 08/479,096 (Richards et al.), filed Jul. 3, 1995 (see especially pages 16–20) and U.S. Pat. No. 5,549,589 (Horney et al.), issued Aug. 27, 1996 (see especially Columns 9 to 10). The disclosures of both of these references are incorporated by reference herein.

The absorbent layer can also comprise a HIPE-derived hydrophilic, polymeric foam that does not have the high absorbency of those described above as "superabsorbent materials". Such foams and methods for their preparation are described in U.S. Pat. No. 5,550,167 (DesMarais), issued Aug. 27, 1996; and commonly assigned U.S. patent application Ser. No. 08/370,695 (Stone et al.), filed Jan. 10, 1995 (both of which are incorporated by reference herein).

The absorbent layer of the cleaning pad can be comprised of a homogeneous material, such as a blend of cellulosic fibers (optionally thermally bonded) and swellable superabsorbent gelling polymer. Alternatively, the absorbent layer can be comprised of discrete layers of material, such as a layer of thermally bonded airlaid material and a discrete layer of a superabsorbent material. For example, a thermally bonded layer of cellulosic fibers can be located lower than (i.e., beneath) the superabsorbent material (i.e., between the superabsorbent material and the scrubbing layer). In order to achieve high absorptive capacity and retention of fluids under pressure, while at the same time providing initial delay in fluid uptake, it can be preferable to utilize such discrete layers when forming the absorbent layer. In this regard, the superabsorbent material can be located remote from the scrubbing layer by including a less absorbent layer as the lower-most aspect of the absorbent layer. For example, a layer of cellulosic fibers can be located lower (i.e., beneath) than the superabsorbent material (i.e., between the superabsorbent material and the scrubbing layer).

In a preferred embodiment, the absorbent layer comprises a thermally bonded airlaid web of cellulose fibers (Flint River, available from Weyerhaeuser, Wash.) and AL Thermal C (thermoplastic available from Danaklon a/s, Varde, Denmark), and a swellable hydrogel-forming superabsorbent polymer. The superabsorbent polymer is preferably incorporated such that a discrete layer is located near the surface of the absorbent layer which is remote from the scrubbing layer. Preferably, a thin layer of, e.g., cellulose fibers (optionally thermally bonded) are positioned above the superabsorbent gelling polymer to enhance containment.

The scrubbing layer is the portion of the cleaning pad that contacts the soiled surface during cleaning. As such, materials useful as the scrubbing layer must be sufficiently durable that the layer will retain its integrity during the cleaning process. In addition, when the cleaning pad is used in combination with a solution, the scrubbing layer must be capable of absorbing liquids and soils, and relinquishing those liquids and soils to the absorbent layer. This will ensure that the scrubbing layer will continually be able to remove additional material from the surface being cleaned. Whether the implement is used with a cleaning solution (i.e., in the wet state) or without cleaning solution (i.e., in the dry state), the scrubbing layer will, in addition to removing particulate matter, facilitate other functions, such as polishing, dusting, and buffing the surface being cleaned.

The scrubbing layer can be a mono-layer, or a multi-layer structure one or more of whose layers can be slitted to facilitate the scrubbing of the soiled surface and the uptake of particulate matter. This scrubbing layer, as it passes over the soiled surface, interacts with the soil (and cleaning solution when used), loosening and emulsifying tough soils and permitting them to pass freely into the absorbent layer of the pad. The scrubbing layer preferably contains openings (e.g., slits) that provide an easy avenue for larger particulate soil to move freely in and become entrapped within the absorbent layer of the pad. Low density structures are preferred for use as the scrubbing layer, to facilitate transport of particulate matter to the pad's absorbent layer.

In order to provide desired integrity, materials particularly suitable for the scrubbing layer include synthetics such as polyolefins (e.g., polyethylene and polypropylene), polyesters, polyamides, synthetic cellulosics (e.g., Rayon®), and blends thereof. Such synthetic materials can be manufactured using known process such as carded, spunbond, meltblown, airlaid, needle punched and the like.

Cleaning pads of the present invention optionally have an attachment layer that allows the pad to be connected to an implement's handle or the support head in preferred implements. The attachment layer will be necessary in those embodiments where the absorbent layer is not suitable for attaching the pad to the support head of the handle. The attachment layer can also function as a means to prevent fluid flow through the top surface (i.e., the handle-contacting surface) of the cleaning pad, and can further provide enhanced integrity of the pad. As with the scrubbing and absorbent layers, the attachment layer can consist of a mono-layer or a multi-layer structure, so long as it meets the above requirements.

The attachment layer can comprise a surface which is capable of being mechanically attached to the handle's support head by use of known hook and loop technology. In such an embodiment, the attachment layer will comprise at least one surface which is mechanically attachable to hooks that are permanently affixed to the bottom surface of the handle's support head.

To achieve the desired fluid imperviousness and attachability, it is preferred that a laminated structure comprising, e.g., a meltblown film and fibrous, nonwoven structure be utilized. In a preferred embodiment, the attachment layer is a tri-layered material having a layer of meltblown polypropylene film located between two layers of spun-bonded polypropylene.

Method of Use—Instructions for use are rendered in consumer-friendly language on the packaging and/or advertising (e.g., leaflets, coupons, displays, etc.). By consumer-friendly language, it is meant that consumers would be instructed how to preferably use the product, e.g., "apply five sprays of product over a two square foot area", to achieve best results. The units of measurement provided to consumers will reflect consumer understanding, e.g., English dosing units will be preferred in the United States, and metric units will be used in most other geographies. Pictures can be used, either with, or without, words in helping make the instructions consumer-friendly. Special packaging design can also be advantageously used to convey instructions in a consumer-friendly fashion. Ergonomic appeal can also make product use more intuitive, either with or without words and pictures. In particular, the packaging can be designed to facilitate proper dispensing. Although all of the following methods described herein (below) are written in metric units; it is understood that these units will be converted into consumer-friendly language instructions in the actual product packaging, advertising etc., as illustrated above.

Floor Cleaning Using a Disposable Pad—Optionally, and most preferably, convenience and performance can be maximized by using a system composed of a disposable cleaning pad and a mode for applying fresh solution onto the floor. The pad is composed of a laminate of non-wovens, cellulose and super-absorbent polymer. This pad is attached to a device comprising a mop head and handle. In such a system, solution application can be achieved via a separate squirt bottle or spray trigger system, or can be directly attached or built-in to the device (i.e., on the mop head or the handle). The delivery mechanism can be actuated by the operator, or can be battery-induced or electrical.

This system provides multiple benefits versus conventional cleaning modes. It reduces time to clean the floor, because the pad sucks up dirty solution. It eliminates the need to carry heavy, messy buckets. Due to the absorbent pad which absorbs and locks away dirty solution, a single pad can clean large surface areas.

Additionally, since a fresh pad is used every time, germs and dirt are trapped, removed and thrown away, promoting better hygiene and malodor control. Conventional mops, which are re-usable, can harbor dirt and germs, which can be spread throughout the household and create persistent bad odors in the mop and in the home. Through operator-controlled dosing and more efficient removal of dirty solution from the floor, better end result is also achieved.

Additionally, because the cleaning process involves use of low levels of solution in contact with the floor for much shorter periods of time relative to conventional cleaning systems, (less solution is applied on the floor and the super-absorbent polymer absorbs most of it such that volume left behind with the disposable pad and mop is only from about 1 to about 5 milliliters of solution per square meter), the system provides improved surface safety on delicate surfaces. This is particularly important for the cleaning of wood, which tends to expand and then when excess treated with excess water.

Finally, this system is well suited for pre-treating tough soil spots prior to full floor cleaning because of the controlled dosing of solution. Unlike conventional mops, this system is more effective and more convenient for removal of spills. For example, conventional mops actually wet the floor in attempting to control spills, while absorbent paper towels or cloths require the user to bend down to achieve spill removal. Finally, the implement plus pad can be designed to allow easy access to tough to clean and hard to reach areas, e.g., under appliances, tables, counters, and the like. The use of super-absorbent polymer allows a reduction in volume of the pad, i.e., the pad is thin though highly absorbent due to the super-absorbent structure being able to absorb 100 times its weight; this is achievable with conventional mops, which require greater bulk for absorption purposes (cellulose or a synthetic structures absorb only up to about from 5 to about 10 times their weight).

For best results using the disposable pad and implement cleaning system, first thoroughly sweep and/or vacuum before wet mopping. Prior to application of the solution to the areas to be cleaned, preferably apply from about 10 to about 20 milliliters in small area (e.g., about one-half a square meter) and wipe pad across area back and forth several times until solution is almost completely absorbed. This is important in that it primes the pad, allowing it to function most effectively. In an application where the dosing mechanism is separate from the implement (i.e., a detached dosing system), a priming set can optionally be to spray solution directly onto the pad, with even coverage using from about 10 to about 20 milliliters. Apply solution at rate of from about 5 to about 40 milliliters, more preferably from about 10 to about 30 milliliters per square meter, spreading the liquid out as much as possible over the area section to be cleaned. This is followed by wiping using the disposable pad.

A preferred wiping pattern consists of an up-and-down overlapping motion starting in the bottom left hand (or right hand) side of the section to be cleaned, and progressing the wiping pattern across the floor continuing to use up-and-down wiping motions. Wiping is then continued beginning at the top right (or left) side of the section to be cleaned and reversing the direction of the wipe pattern using a side-to-side motion. Another preferred wipe pattern consists of an up-and-down wiping motion, followed by an up-and-down wiping motion in the reverse direction. These thorough preferred wiping patterns allow the pad to loosen and absorb more solution, dirt and germs, and provide a better end result in doing so by minimizing residue left behind. Another benefit of the above wiping patterns is minimization of streaks as a result of improved spreading of solution and the elimination of streak lines from the edges of the pad.

The pads are versatile in that they can be used for multiple cleanings and multiple surfaces. Each pad is designed to clean one average size floor (i.e., from about 10 to about 20 square meters) with an average soil load. Pads can need to be changed sooner if floors are larger than average, or especially dirty. To determine if the pad needs changing, look at the back of the pad and ascertain if the back absorbent layer is saturated with liquid and/or dirt.

The use of the compositions herein, where no rinsing is desirable, as opposed to the types of compositions sold heretofore for treating non-bathtub/shower area surfaces including floor surfaces, walls and counter tops, provides improved performance.

The following are non-limiting examples of the compositions and kits of the present invention.

EXAMPLES

Example 1

Compositions
Wt. % in Aqueous Solution

| Ingredient | A | B | C | D | E | F | G | H | I |
|---|---|---|---|---|---|---|---|---|---|
| Surfactant[1] | 0.005 | 0.001 | 0.02 | 0.001 | — | 0.03 | 0.09 | 0.05 | 0.01 |
| Soil Entrainment System[2] | 0.015 | 0.05 | 0.002 | 0.02 | 0.04 | 0.009 | 0.004 | 0.03 | 0.02 |
| Buffer[3] | 0.2 | 0.01 | 0.06 | 0.09 | 0.1 | 0.16 | 0.02 | 0.01 | — |
| Solvent[4] | 4.0 | 3.0 | 2.0 | 1.0 | — | 4.0 | 0.9 | 2.0 | 4.0 |
| Perfume[5] | 0.008 | 0.03 | 0.06 | 0.006 | 0.02 | 0.055 | 0.08 | — | 0.06 |
| Suds Suppressor | 0.001 | — | 0.002 | — | — | 0.002 | 0.003 | 0.001 | — |
| Antimicrobial[6] | 0.001 | 0.015 | 0.03 | — | 0.02 | 0.022 | 0.04 | 0.03 | — |
| Water and minors (dye, etc.) up to 100% | q.s. | q.s. | q.s. | q.s. | q.s. | q.s. | q.s. | q.s. | q.s. |

[1]Selected from Neodol 11-5, Nonidet CF-3, Nonidet CF-5, (all Shell Chemical), C8 sulfonate (Witconate NA-8) C11-18 APG (Henkel), Fluorad F170 (3M) and mixtures thereof, such as, Neodol 11-5 and C8 sulfonate.
[2]Selected from Lupasol SK or SKA, Sedipur CF803, PEG (av. mwt 800,000 daltons)
[3]Selected from: 2-dimethylamino-2-methylpropanol (DMAMP), ammonia, and 1,3-bis(methylamine)-cyclohexane.
[4]Selected from ethanol, propanol, isopropanol, propoxypropanol, methoxypropanol, ethoxypropanol, ethoxybutanol and mixtures thereof, such as, isopropanol and propoxypropanol.
[5]Dow Corning silicone suds supressor
[6]Selected from Chlorhexidine digluconte, methylbenzethonium chloride, Dodecyltriphenyphosphonium bromide, Didecyldimethylammonium chloride (Bardac 2250, Lonza).

Example 2

Kit

A kit is prepared in a container. The composition of 1(a) is included in the kit in a bottle. The kit also includes an implement, such the implements describe in copending application 60/061,296, filed Oct. 7, 1997 by N. J. Policicchio, et al. (P&G Case 6873P). Instructions for assembling the implement and removal and replacement of the superadsorbent sponges are included in the kit. Instructions for using the implement in combination with the cleaning solution to clean floors is also included. All the components of the kit are contained in a readily accessible and easy to open carrying package.

Example 3

Hazing and Streaking Test
Soil and Tile Preparation:

Single Tile Performance Test—Strip the test tile with a mixture of 2-propanol/DI water (20:80) followed by acetone prior to using the tile. Buff the tile with a lint-free cloth (kimwipe) to remove any streaks or dust. Mix pre-made soil solution (see below) on a mechanical stir plate to ensure a homogenous mixture. On a separate tile prime a 3 inch paint roller with 2 milliliters of the soil solution. Apply 1.5 milliliters of the soil solution to the test tile and distribute evenly over the entire surface with the primed paint roller. Allow the soil solution to dry on the test tile for approx. 30 minutes. Attach a new cleaning pad to the hand held implement and on a separate tile use 1.25 milliliters of cleaning solution to prime (wet) the pad. Apply 2.5 milliliters of cleaning solution to the soiled test tile. Clean the test tile with the primed pad and implement using 10 strokes from the left side of the tile to the right side of the tile followed by 10 strokes in the reverse direction. A stroke is defined as moving the pad across the tile surface in a straight line from the bottom to the top and back to the bottom. Allow the test tile to completely dry and wipe one corner of the tile with the 2-propanol/DI water mixture to remove any remaining particulate and/or streaks. Grade the test tile for streaks and haze using the grading scale below.

| Particulate Soil: Component | Percentage |
|---|---|
| acetone | 9.747% |
| palmitic acid | 0.017% |
| stearic acid | 0.007% |
| chemically altered beef fat | 0.009% |
| 2-propanol | 88.02% |
| sifted clay (EMC) | 0.978% |
| Black Todd clay (EMC) | 0.978% |
| vacuum cleaner soil (EMC) | 0.245% |

Streaks grading scale is 0–4

0—No streaks

1—Slight streaks

2—Moderate to heavy streaks

3—Heavy streaks

4—Severe streaks

Haze grading scale is 0–3 based on the difference between the tile and the stripped corner 0—No haze 0.5—No to light haze 1.0—Light haze 1.5—Light to moderate haze 2.0—Moderate haze 2.5—Moderate to heavy haze
3.0—Heavy haze Test one

| Buffer: | 2-dimethylamino-2-methylpropanol | 0.06% |
|---|---|---|
| Soil Entrainment System | Polyethylene glycol av. Mwt. 5,000,000 Daltons | 0.02% |
| nonionic surfactant | C11E5 | 0.09% |
| anionic surfactant | C8 sulfonate anionic | 0.05% |
| Leveling agent | Xanthum gum | 0.005% |
| Suds supressor | Dow Corning silicone suds supressor | 0.00125% |
| Water and minors (dye etc.) up to 100% | | q.s. |

Results:

| Streaks | Haze |
|---|---|
| 0.5 | 0.5 |

Test two:
Formulation Tested

| Buffer: | 1,3-bis(methylamine)-cyclohexane | 0.3% |
|---|---|---|
| Surfactants: | | |
| Nonionic | C11EO5 nonionic | 0.02% |
| Anionic | C8 sulfonate anionic | 0.01% |
| Water and minors (dye etc.) up to 100% | | q.s. |

Polymer is a Polyethylene glycol with an average molecular weight of 2,000,000 Daltons.

| | Streaks | Haze |
|---|---|---|
| without Soil Entrainment System | 2.25 | 2.0 |
| Soil Entrainment System (0.02%) | 1.25 | 1.25 |

Test 3
Formulation tested

| Buffer: | 2-dimethylamino-2-methylpropanol | 0.01% |
|---|---|---|
| Solvent | propoxypropanol | 2.0% |
| Suds Supressor | Dow Corning silicone suds supressor | 0.00125% |
| Surfactants: | | |
| Nonionic | C11EO5 nonionic | 0.02% |
| Anionic | C8 sulfonate anionic | 0.01% |
| Water and minors (dye etc.) up to 100% | | q.s. |

Polymer is Lupasol SK with an average molecular weight of 800,000 Daltons.

| | Streaks | Haze |
|---|---|---|
| without Soil Entrainment System | 2.0 | 1.5 |
| Soil Entrainment System (0.02%) | 0.5 | 0.375 |

What is claimed is:

1. An aqueous liquid hard surface cleaning composition that provides effective cleaning and good filming streaking, in combination with a disposable cleaning pad, said combination being suitable for use without rinsing wherein said composition comprises:
   a) from about 0.001% to about 1.5%, by weight, of a soil entrainment system, said soil entrainment system is selected from the group consisting of
      1) one or more modified polyamine compounds, said modified polyamine compounds are selected from:
         i) $(PA)_w(T)_x$;
         ii) $(PA)_w(L)_z$;
         iii) $[(PA)_w(T)_x]_y[L]_z$; and
         iv) mixtures thereof;
         wherein PA is a grafted or non-grafted, modified or unmodified polyamine backbone unit, T is an amide-forming polycarboxylic acid crosslinking unit, and L is a non-amide forming crosslinking unit; provided that for compounds of type (i) and (iii) the indices w and x have values such that the ratio of w to x is from 0.8:1 to 1.5:1; for compounds of type (ii) the indices w and z have values such that said modified polyamine compound comprises from about 0.05 to about 2 parts by weight of said L unit; for compounds of type (iii) the indices y and z have values such that said modified polyamine compound comprises from about 0.05 to about 2 parts by weight of said L unit;
      2) one or more modified polyacrylamide compounds of the formula:

$$-[CR_2-CR_2]_n-$$

wherein each R unit is independently selected from the group consisting of hydrogen, $C_1$–$C_{12}$ alkyl, $C_6$–$C_{12}$ aryl, $CON(R')_2$, and D; wherein each D unit is independently selected from the group consisting of $CO_2N(R')_m$, $CON(R')CH_2CON(R')_2$, $OCON(R')_2$, and $CO_2(CH_2)_qN(R')_m$, wherein each R' is selected from the group consisting of hydrogen, $C_1$–$C_{12}$ alkyl, or both R' units can be taken together to form a ring comprising 4–6 carbon atoms; q is an integer from 0 to 5; m is either 2 or 3 and n is a number selected such that said modified polyacrylamide compounds have an average molecular weight of from about 20,000 Daltons to about 10,000,000 Daltons;
      3) mixtures thereof;
   b) from about 0.001% to about 0.2%, by weight, of a surfactant; and
   c) the balance adjunct ingredients;
wherein said composition has a pH under usage conditions of from about 2 to about 12.

2. A composition according to claim 1 wherein said PA polyamine backbone unit comprises a polyamine which is grafted wherein said grafting agent is selected from aziridine, caprolactam, and mixtures thereof.

3. A composition according to claim 1 wherein said T unit has the formula:

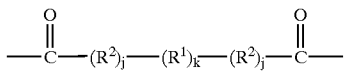

wherein R' is methylene, phenylene, and mixtures thereof; $R^2$ is —NH—; k is from 2 to 8, each j is independently 0 or 1.

4. A composition according to claim 1 wherein said L unit is selected from:

i) polyalkylene units having the formula:

wherein n is from 1 to about 50;

ii) epihalohydrin/polyalkylene units having the formula:

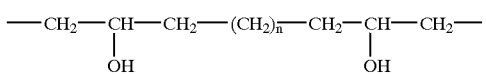

wherein n is from 1 to 50;

iii) polyalkyleneoxy comprising units having the formula:

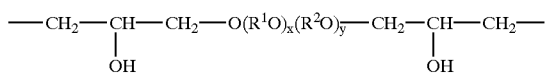

wherein R' is ethylene, $R^2$ is 1,2-propylene, x is from 0 to 100 and y is from 0 to 100;

iv) polyhydroxy comprising units having the formula:

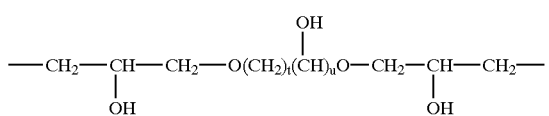

wherein the index t is at least 2 and the index u is from 1 to about 6;

v) polyalkyleneoxy/polyhydroxy comprising units having the formula:

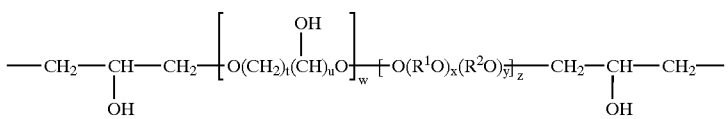

wherein $R^1$, $R^2$, t, u, x, and y are the same as defined above, the indices w and z are each independently from 1 to 50;

vi) units which comprise an aziridine unit having the formula:

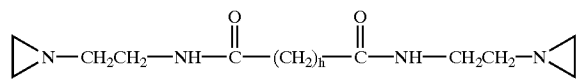

wherein h is from 0 to 22; and vii) mixtures thereof.

5. A composition according to claim 1 wherein said polyamine compound is formed by the reaction of:
 a) 1 part by weight, of a polyamidoamine obtained by condensation of 1 mole of a dicarboxylic acid with from 0.8 to 1.5 moles of a polyalkylene polyamine then optionally reacting the obtained polyamidoamine condensation product with up to 8 ethyleneimine units per basic nitrogen atom; and
 b) further reacting the product obtained in (a) with from 0.05 to 2 parts by weight, of a reaction product of a polyalkylene oxide having from 8 to 100 alkylene oxide units with epichlorohydrin at a temperature of form about 20° C. to about 100° C.

6. The composition of claim 1 wherein said R is independently selected from the group consisting of $C_1$–$C_4$ alkyl, hydrogen, D and $CON(R')_2$.

7. The composition of claim 6 wherein said D is selected from the group consisting of $CO_2(CH_2)_qN(R')_3$, wherein q is an integer from 0 to 5.

8. The composition of claim 1 wherein said adjunct ingredients are selected from the group consisting of surfactants, buffers, enzyme, solvent, perfume, suds suppressor, antimicrobial agents, and mixtures thereof.

9. The composition of claim 8 wherein said antimicrobial agents are selected from the group consisting of quaternary amines, chlorhexidine digluconte, methylbenzonium chloride, dodecyltriphenylphosphonium bromide, didecyldimethylamonium chloride and mixtures thereof.

10. The composition of claim 8 wherein said solvent is selected from the group consisting of: mono-propylene glycol mono-propyl ether, mono-propylene glycol mono-butyl ether, di-propylene glycol mono-propyl ether di-propylene glycol mono-butyl ether, di-propylene glycol mono-butyl ether; tri-propylene glycol mono-butyl ether; ethylene glycol mono-butyl ether; diethylene glycol mono-butyl ether, ethylene glycol mono-hexyl ether and diethylene glycol mono-hexyl ether, methanol, ethanol, isopropanol, n-butanol, iso-butanol, pentanol, 2-methyl-1-butanol, 2-butanone, methoxymethanol, methoxyethanol, methoxy propanol, ethoxypropanol, propoxypropanol, ethoxybutanol and mixtures thereof.

11. The composition of claim 8 wherein to minimize streaking/filming problems, the buffering is provided, at least in part, by volatile materials whose molecular weight is less than about 400 g/mole.

12. The composition of claim 8 wherein said buffer is selected from the group consisting of ammonium hydroxide, 2-dimethylamino-2-methyl-1-propanol, acetic acid, amonium carbamate, monoethanolamine, diethanolamine, triethanolamine, alkali metal carbonate, alkali metal phosphate, lysine, Tri(hydroxymethyl)amino methane, 1,3-bis(methylamine)-cyclohexane and mixtures thereof.

13. The composition of claim 8 wherein said surfactant is selected from the group consisting of anionic, nonionic, zwitterionic, amphoteric and mixtures thereof.

14. The detergent composition of claim 13 wherein said surfactant is selected from the group consisting of alkyl polyoxyalkylene, flourinated nonionic surfactants, silicone surfactants, C8 to C12 alkyl sulfonate, alkylpolyglucosides and mixtures thereof.

15. The process of cleaning a hard surface comprising applying an effective amount of the cleaning composition of claim 1 to said hard surface and absorbing the composition in an absorbent structure comprising a superabsorbent material.

16. A kit comprising an implement containing a pad containing superabsorbent material and a detergent composition that provides effective cleaning and good filming streaking when used with a disposable cleaning pad and without rinsing wherein said composition comprises:
(a) from about 0.001% to about 1.5%, by weight of a soil entrainment system, said soil entrainment system is selected from the group consisting of
(1) one or more modified polyamine compounds, said modified polyamine compounds are selected from:
  (i) $(PA)_w(T)_x$;
  (ii) $(PA)_w(L)_z$; or
  (iii) $[(PA)_w(T)_x]_y[L]_z$; and
  (iv) mixtures thereof;
wherein PA is a grafted or non-grafted modified or unmodified polyamine backbone unit, T is an amide forming polycarboxylate crosslinking unit, and L is a non-amide forming crosslinking. unit, provided that for compounds of type (i) and (iii) the indices w and x have values such that the ratio of w to x is from 0.8:1 to 1.5:1; for compounds of type (ii) the indices w and z have values such that said modified polyamine compounds comprises from about 0.05 to about 2 parts by weight of said L unit; for compounds of type (iii) the indices y and z have values such that said modified polyamine compound comprises from about 0.05 to about 2 parts by weight of said L unit;
2) one or more modified polyacrylamide compounds of the formula:

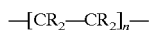

wherein each R unit is independently selected from the group consisting of hydrogen, $C_1$–$C_{12}$ alkyl, $C_6$–$C_{12}$ aryl, $CON(R')_2$, and D; wherein each D unit is independently selected from the group consisting of $CO_2N(R')_m$, $CON(R')CH_2CON(R')_2$, $OCON(R')_2$, and $CO_2(CH_2)_qN(R')m$, wherein each R' is selected from the group consisting of hydrogen, $C_1$–$C_{12}$ alkyl, or both R' units can be taken together to form a ring comprising 4–6 carbon atoms; q is an integer from 0 to 5; m is either 2 or 3 and n is a numbers selected such that said modified polyacrylamide compounds have an average molecular weight of from about 20,000 Daltons to about 10,000,000 Daltons; and
3) mixtures thereof;
b) from about 0.001% to about 0.2%, by weight, of a surfactant; and
c) the balance adjunct ingredients;
wherein said composition has a pH under usage conditions of from about 2 to about 12.

17. A kit according to claim 16 wherein said PA polyamine backbone unit comprises a polyamine which is grafted wherein said grafting agent is selected from aziridine, caprolactam, and mixtures thereof.

18. A kit according to claim 16 wherein said T unit has the formula:

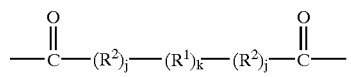

wherein R' is methylene, phenylene, and mixtures thereof; $R^2$ is —NH—; k is from 2 to 8, each j is independently 0 or 1.

19. A kit according to claim 16 wherein said L unit is selected from:
i) polyalkylene units having the formula:

wherein n is from 1 to about 50;
ii) epihalohydrin/polyalkylene units having the formula:

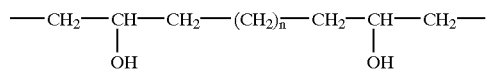

wherein n is from 1 to 50;
iii) polyalkyleneoxy comprising units having the formula:

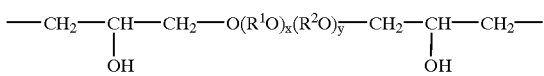

wherein $R^1$ is ethylene, $R^2$ is 1,2-propylene, x is from 0 to 100 and y is from 0 to 100;
iv) polyhydroxy comprising units having the formula:

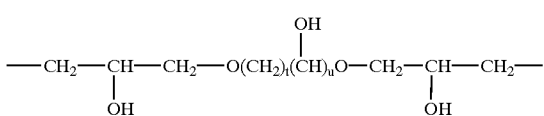

wherein the index t is at least 2 and the index u is from 1 to about 6;
v) polyalkyleneoxy/polyhydroxy comprising units having the formula:

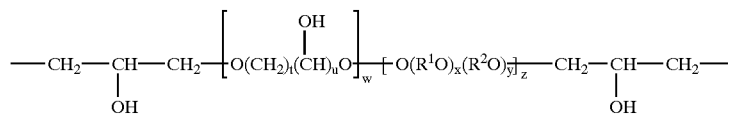

wherein $R^1$, $R^2$, t, u, x, and y are the same as defined above, the indices w and z are each independently from 1 to 50;

vi) units which comprise an aziridine unit having the formula:

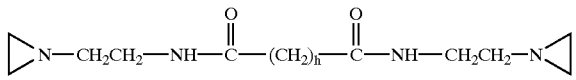

wherein h is from 0 to 22; and vii) mixtures thereof.

20. A kit according to claim 16 wherein said polyamine compound is formed by the reaction of:
  a) 1 part by weight, of a polyamidoamine obtained by condensation of 1 mole of a dicarboxylic acid with from 0.8 to 1.5 moles of a polyalkylene polyamine then optionally reacting the obtained polyamidoamine condensation product with up to 8 ethyleneimine units per basic nitrogen atom; and
  b) further reacting the product obtained in (a) with from 0.05 to 2 parts by weight, of a reaction product of a polyalkylene oxide having from 8 to 100 alkylene oxide units with epichlorohydrin at a temperature of form about 20° C. to about 100° C.

21. The kit according to claim 16, wherein said R is independently selected from the group consisting of $C_1$–$C_4$ alkyl, hydrogen, D and $CON(R')_2$.

22. The kit according to claim 21, wherein said D is selected from the group consisting of $CO_2(CH_2)_q N(R')_3$, wherein q is an interger from 0 to 5.

23. The kit according to claim 16, wherein said pad is detachably mounted on said implement.

24. The kit according to claim 16 further comprising instructions for use of said kit in association with said composition and said implement to insure optimum usage.

25. The kit according to claim 16 wherein the back of said pad has words and/or pictures explaining which side of said pad to attach to implement.

26. The kit according to claim 16 wherein said implement further comprises a dosing device, said dosing device delivers said detergent composition to the surface to be cleaned.

27. The kit of claim 26 wherein said dosing device is battery or electrically powered and applies continuous flow such that the number of sprays is defined by the number of seconds to hold dispensing the trigger or button.

28. The kit according to claim 16 wherein said implement further comprises a reservoir, said reservoir holds said cleaning solution.

29. The kit of claim 28 wherein said reservoir is detachably mounted on said implement.

30. The kit of claim 16 wherein said pad comprises an inner absorbent core with super-absorbent polymer and outer scrub layer made of an apertured formed film.

31. The kit of claim 16 wherein said adjunct ingredients are selected from the group consisting of surfactants, buffers, enzyme, solvent, perfume, suds suppressor, antimicrobial agents, and mixtures thereof.

32. A process according to claim 15 which is conducted without a rinsing step.

* * * * *